United States Patent
Kulik et al.

(10) Patent No.: US 7,492,859 B2
(45) Date of Patent: Feb. 17, 2009

(54) BUILDUP-ROBUST DENSITY, LEVEL AND INTERFACE MEASUREMENT WITH γ-BACKSCATTERING

(75) Inventors: Alex Kulik, Sugar Land, TX (US); Alexander Joseph Esin, Sugar Land, TX (US); Nikolay Baturin, Sugar Land, TX (US)

(73) Assignee: Thermo Fisher Scientific Inc., Sugar Land, TX (US)

( * ) Notice: Subject to any disclaimer, the term of this patent is extended or adjusted under 35 U.S.C. 154(b) by 0 days.

(21) Appl. No.: 12/054,215

(22) Filed: Mar. 24, 2008

(65) Prior Publication Data

US 2008/0226026 A1 Sep. 18, 2008

Related U.S. Application Data

(63) Continuation of application No. 11/598,559, filed on Nov. 13, 2006.

(51) Int. Cl.
G01B 15/02 (2006.01)
(52) U.S. Cl. .............................. 378/54; 378/57; 378/86; 378/89
(58) Field of Classification Search .................. 378/51, 378/54, 57, 58, 59, 70, 86, 89
See application file for complete search history.

(56) References Cited

U.S. PATENT DOCUMENTS

| | | | |
|---|---|---|---|
| 3,832,545 A | 8/1974 | Bartko | 376/159 |
| 4,582,991 A | 4/1986 | Leonardi-Cattolica et al. | 250/358.1 |
| 4,817,021 A | 3/1989 | Sowerby et al. | 702/137 |
| 4,870,278 A | 9/1989 | Leonardi-Cattolica et al. | 250/357.1 |
| 5,400,381 A * | 3/1995 | Steude et al. | 378/57 |
| 6,362,477 B1 | 3/2002 | Sowerby et al. | 250/358.1 |
| 2006/0133566 A1 | 6/2006 | Li et al. | |
| 2008/0112536 A1* | 5/2008 | Kulik et al. | 378/89 |

OTHER PUBLICATIONS

U.S. Office Action issued in corresponding U.S. Appl. No. 11/598,559; dated Sep. 06, 2007; 8 pages.
U.S. Office Action issued in corresponding U.S. Appl. No. 11/598,559; dated May 30, 2008; 11 pages.

\* cited by examiner

*Primary Examiner*—Courtney Thomas
(74) *Attorney, Agent, or Firm*—Osha • Liang LLP

(57) ABSTRACT

System and methods for measuring the density, level, or interface position of a fluid or fluids in a vessel using gamma-ray backscatter are disclosed. The gamma-ray instruments disclosed may account for vessel wall buildup or deterioration. Methods disclosed herein include detecting gamma rays backscattered by a fluid from a gamma-ray source positioned proximate to a vessel with at least two gamma-ray detectors positioned proximate to the vessel and to each other; and determining a density, level, or interface value of the fluid based upon intensities of backscattered gamma rays received by the two or more gamma-ray detectors; wherein the vessel wall is subject to at least one of buildup and deterioration. The density, level, or interface may be a function of a ratio of the intensity of backscattered gamma rays received by two or more of the detectors.

46 Claims, 8 Drawing Sheets

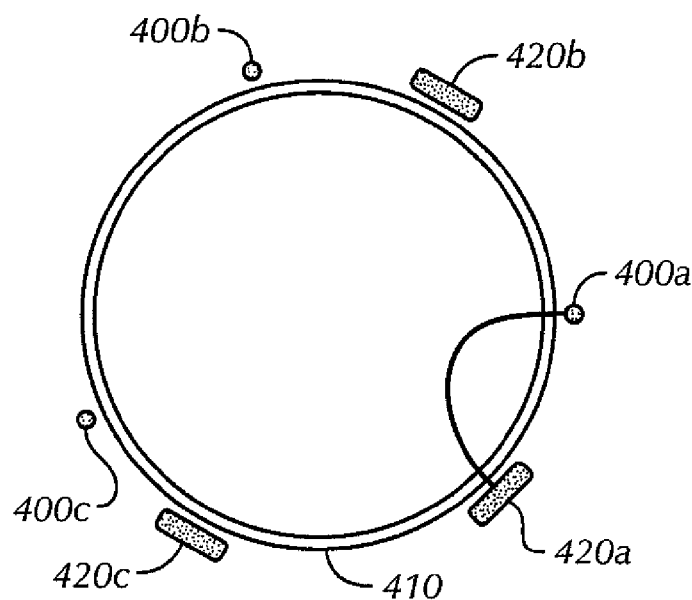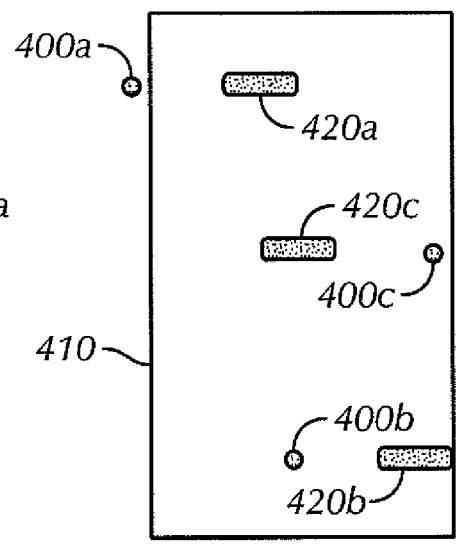
FIG. 9a          FIG. 9b
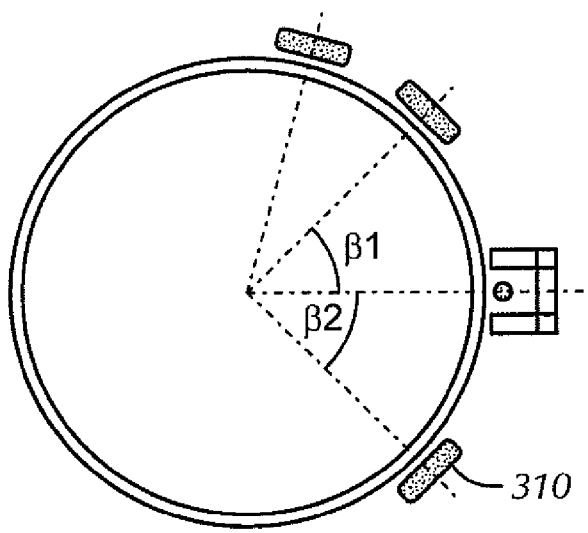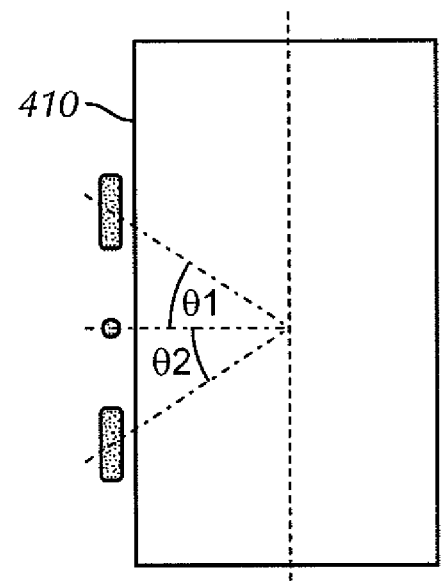
FIG. 10a         FIG. 10b

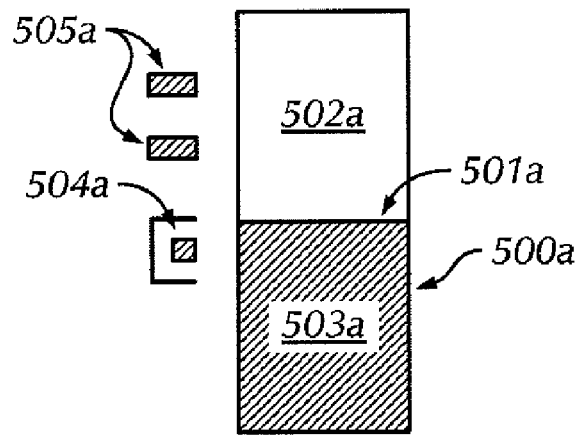 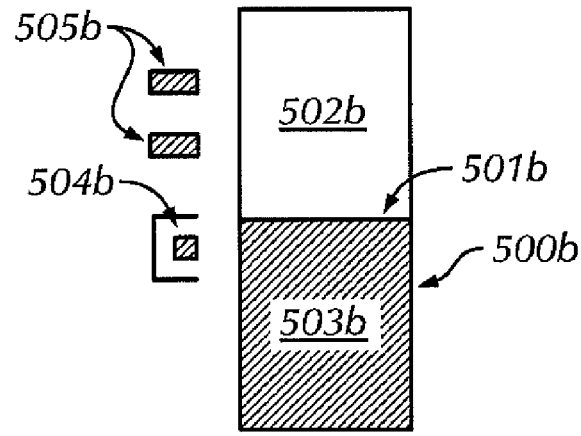
FIG. 13a    FIG. 13b
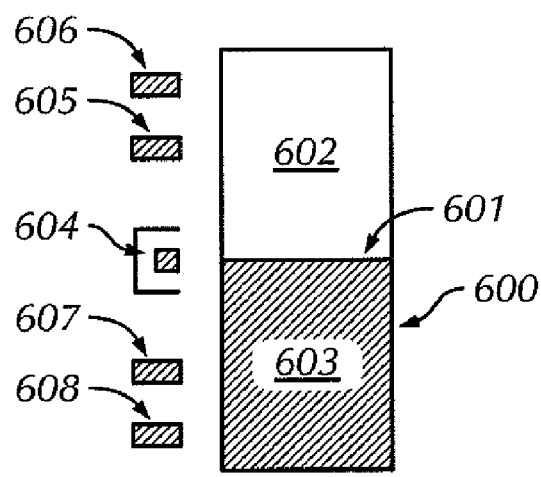
FIG. 14

BUILDUP-ROBUST DENSITY, LEVEL AND INTERFACE MEASUREMENT WITH γ-BACKSCATTERING

CROSS-REFERENCE TO RELATED APPLICATIONS

The present application is a Continuation-in-Part and claims the benefit, pursuant to 35 U.S.C. § 120, of U.S. patent application Ser. No. 11/598,559 filed on Nov. 13, 2006, currently pending, which is incorporated by reference in its entirety herein.

BACKGROUND OF INVENTION

1. Field of the Invention

Embodiments disclosed herein relate generally to the measurement of the density, level and/or interface of a fluid in a vessel using gamma radiation. Specifically, embodiments disclosed herein relate to the measurement of the density, level and/or interface of a fluid in a vessel by detecting the intensity of gamma rays backscattered by the fluid from a gamma-ray source.

2. Background

Gamma rays have been used to measure the density, level and interface of fluids in a vessel by using a gamma-ray source positioned opposite a gamma-ray detector. These through-transmission gamma-ray density and level measurements are useful where the materials measured are hazardous, extremely hot, or where direct contact measurements are otherwise not possible. Additionally, the source and detector are mounted outside the vessel, and no modification to the vessel is required. Gamma rays emitted by a source may be absorbed or attenuated by the vessel and the material in the vessel. The strength of the gamma radiation reaching a detector opposite the source may be used to indicate the density, level and/or interface of a fluid in a vessel based upon the intensity of the source.

When measuring fluid level, for example, multiple gamma-ray emitters and/or detectors may be positioned at opposite sides of a vessel, where the presence or absence of a signal (or a nominal low signal) may indicate the presence or absence of a fluid in place between the source and detector. The size of a vessel in a signal/no signal level detector may be much larger than that for a gamma-ray densitometer, as described below, as gamma rays are not as readily absorbed or attenuated by vapors in the vessel.

With respect to fluid interface, for example, multiple gamma-ray emitters and/or detectors may be positioned at opposite sides of a vessel. One or more of the two types of fluids passing between the source and the detector may absorb or attenuate gamma rays emitted by the source. As the densities of the two types of fluids differ, a radiation count indicates the relative amounts of the low-density and the high-density fluids, and thus indicates the position of the fluid interface. However, fluid interface measurement using conventional through-transmission technology may be limited to relatively small vessel diameters due to the high amount of absorption and/or attenuation of the gamma-ray signal that increases with the vessel diameter.

With respect to fluid density, for example, fluid passing between the gamma-ray source and detector may absorb or attenuate gamma rays emitted by the source. A high radiation count indicates a low fluid density while a low count indicates a high fluid density. Similar to the fluid interface measurement, density measurement using the conventional through-transmission technology may also be limited to relatively small-diameter vessels.

Referring now to FIG. 1, one example of a prior-art through-transmission gamma-ray densitometer is illustrated. A housing (not shown) may be mounted on a tubular pipe or vessel 10 with a bore 12 which contains a fluid 13. A source of gamma radiation 14 is located on one side of the bore 12 and, a gamma radiation detector 15 is located on an opposite side. The radiation provided by the source 14 is a constant intensity over a long period of time (random intensity over a finite period) of gamma-ray emissions. The gamma rays are transmitted through the material surrounding the bore 12, the fluid 13 within the bore and to the detector 15. The detector 15 may be, for example, a crystal of sodium or cesium iodide (thallium activated) or other material capable of scintillating under irradiation and may include an electron photomultiplier tube for converting light flashes of the scintillation of the crystal into an electrical pulse.

A primary variable with respect to the amount of gamma rays emitted from source 14 that reach detector 15 is fluid 13 contained within vessel 10. A percentage of the gamma rays emitted by source 14 are absorbed or attenuated by fluid 13 and do not reach detector 15. Thus, the counting rate of the output signal from the photo multiplier tube of detector 15 may be related to the density, level and/or interface of fluid 13 through which the rays must pass to reach detector 15 and the intensity of source 14.

However, through-transmission density measurement using gamma rays is viable only for limited vessel sizes and/or fluid densities. For example, for a similar sized source, at higher fluid densities, the fluid may absorb more gamma rays, thus resulting in fewer gamma rays reaching the detector. Similarly, as vessel size is increased, gamma rays must pass through a greater quantity of material (vessel and fluid) absorbing the gamma rays, resulting in fewer gamma rays reaching the detector. Therefore, whereas through-transmission level measurement, where some gamma rays travel through a low-density gas, such as air, can be used in vessels up to 10 meters in diameter, the through-transmission density and/or interface measurements, where gamma rays travel through one or more high-density fluids, are currently only viable for vessels up to about 1 meter in diameter.

Vessel thickness may also limit the effectiveness of through-transmission gamma-ray density, level, and interface measurements. As vessels absorb and attenuate gamma rays in a manner similar to fluids, and a higher wall thickness may result in fewer gamma rays reaching the detector. Vessel thickness may be regulated by code, such as ASME or other vessel specifications, where the required thickness may be based upon operating pressure and the nature of the fluid (corrosive, erosive, reactive, etc.). Furthermore, current safety margins for vessel thickness may increase and may further limit the effectiveness of through-transmission measurements.

As a further complication, material build-up, for example, scale, slag, corroded metal, or polymer, may generate on the inside of the vessel walls over time in certain applications. The build-up increases the total amount of material for the gamma rays to travel through, and thus reduces the counting rate. Further, depending on the nature and configuration of the process, a vessel may experience deterioration of wall thickness, for example, related to corrosion, erosion, or other form of degradation. Contrary to the effects of a build-up, deterioration of wall thickness decreases the total amount of material for the gamma rays to travel though, and thus increases the counting rate. As both wall build-up and deterioration may continuously take place over a number of years, frequently at non-uniform and unpredictable rates, the accuracy of a through-transmission measurement will decrease over time.

Another disadvantage in the present use of gamma rays for through-transmission density, level and interface measurements is that the solid angle subtended by a fixed size detector, and thus the counting rate, scales inversely with the size of the vessel squared. The counting rate n may be approximated by the equation:

$$n \sim \Omega e^{-d/\lambda} \sim (e^{-d/\lambda})/d^2 \qquad (1)$$

where n is the counting rate, d is the vessel diameter, and $\lambda$ is the absorption length which depends on density. For a similar sized detector, a lower count rate may result in a greater rate of error or may require a larger source to maintain a desired accuracy. Alternatively, as vessel size is increased, detector size may be increased to maintain a constant count rate. Regardless, increasing the size of the source and/or the size of the detector will invariably increase costs.

To overcome the thickness, size, and density limitations, the intensity of the gamma-ray source may be increased, thus resulting in a measurable quantity of gamma rays reaching the detector. However, cost, safety, multi-unit effectiveness, and security may each limit the source intensity that may be used. For example, the use of a radioactive source creates personnel safety and environmental concerns and requires lead or tungsten shielding to protect personnel, special handling precautions and equipment, as well as disposal and remediation procedures. Furthermore, because gamma rays are produced from a point source and not a directional source, as the size and number of the sources increase, the amount of shielding material required to contain the radiation in directions other than through the vessel must be increased, thus adding further to the cost.

With respect to multi-unit effectiveness, a chemical plant may desire to use gamma-ray density, level and/or interface gauges on multiple vessels, for example. However, as the number of gages is increased or the intensity of gamma-ray sources is increased to overcome size limitations, cross-talk between gamma-ray sources and detectors on adjacent vessels may occur, resulting in decreased effectiveness and potentially erroneous readings.

Regarding security, due to growing worldwide concerns about the proliferation and possible smuggling or other transport of radioactive nuclear materials, state, local, and national governments regulate facility security requirements based upon the total amount of radioactive material that may be present at a single site. For example, the State of Texas requires additional security measures (e.g., background checks, accessibility, etc.) at facilities where the total Curie count exceeds 27 Curie, where the total Curie count is based upon a sum of all radioactive sources at the facility. Thus, use of larger sources to overcome vessel size limitations may result in an increased need for security at an additional cost.

Accordingly, there exists a need for gamma-ray density, level and/or interface gauges that may be used on larger vessels. Additionally, there exists a need for non-contact density, level and/or interface gauges that require lower intensity radiation sources. Further, there exists a need for non-contact density, level and/or interface gauges that provide accurate reading as the effective wall thickness varies, for example, due to build-up and/or deterioration.

SUMMARY OF THE CLAIMED EMBODIMENTS

In one aspect, embodiments disclosed herein relate to a method to determine a fluid density in a vessel, the method including: detecting gamma rays backscattered by a fluid from a gamma-ray source positioned proximate to a vessel with at least two gamma-ray detectors positioned proximate to the vessel and to each other; and determining a density value of the fluid based upon intensities of backscattered gamma rays received by the two or more gamma-ray detectors; wherein the vessel wall is subject to at least one of buildup and deterioration.

In another aspect, embodiments disclosed herein relate to a method to determine a fluid level in a vessel, the method including: detecting gamma rays backscattered by a fluid from a gamma-ray source positioned proximate to a vessel with at least two gamma-ray detectors positioned proximate to the vessel and to each other; and determining a level value of the fluid based upon intensities of backscattered gamma rays received by the two or more gamma-ray detectors; wherein the vessel wall is subject to at least one of buildup and deterioration.

In another aspect, embodiments disclosed herein relate to a method to determine a fluid interface in a vessel, the method including: detecting gamma rays backscattered by one or more fluids from a gamma-ray source positioned proximate to a vessel with at least two gamma-ray detectors positioned proximate to the vessel and to each other; and determining an interface value of a fluid based upon intensities of backscattered gamma rays received by the two or more gamma-ray detectors; wherein the vessel wall is subject to at least one of buildup and deterioration.

In another aspect, embodiments disclosed herein relate to a system for measuring a fluid level in a vessel, the system including: at least one gamma-ray source positioned proximate to a vessel; at least one gamma-ray detector positioned proximate to the vessel, wherein the at least one gamma-ray detector is configured to detect gamma rays backscattered by the fluid from the at least one gamma-ray source; and a translator for converting the detected gamma-ray backscatter into a level value.

In another aspect, embodiments disclosed herein relate to a system for measuring a fluid interface in a vessel, the system including: at least one gamma-ray source positioned proximate to a vessel; at least one gamma-ray detector positioned proximate to the vessel, wherein the at least one gamma-ray detector is configured to detect gamma rays backscattered by the at least one of the two fluids from the at least one gamma-ray source; and a translator for converting the detected gamma-ray backscatter into an interface value.

Other aspects and advantages of the embodiments disclosed herein will be apparent from the following description and the claims.

BRIEF DESCRIPTION OF DRAWINGS

FIGS. 9a-9b present schematic drawings of a gamma-ray density measurement system using multiple detectors and multiple sources spaced axially according to embodiments disclosed herein.

FIGS. 10a-10b present schematic drawings of a gamma-ray density measurement system using multiple detectors spaced at varied angles from a gamma-ray source according to embodiments disclosed herein.

FIGS. 13a-b present schematic drawings of a gamma-ray fluid level and fluid interface measurement systems, respectively, using two detectors and one source spaced axially according to embodiments disclosed herein.

FIG. 14 is a schematic drawing of a gamma ray fluid level and/or fluid interface measurement system using four detectors and one source spaced axially according to embodiments herein.

DETAILED DESCRIPTION

Figure 1:
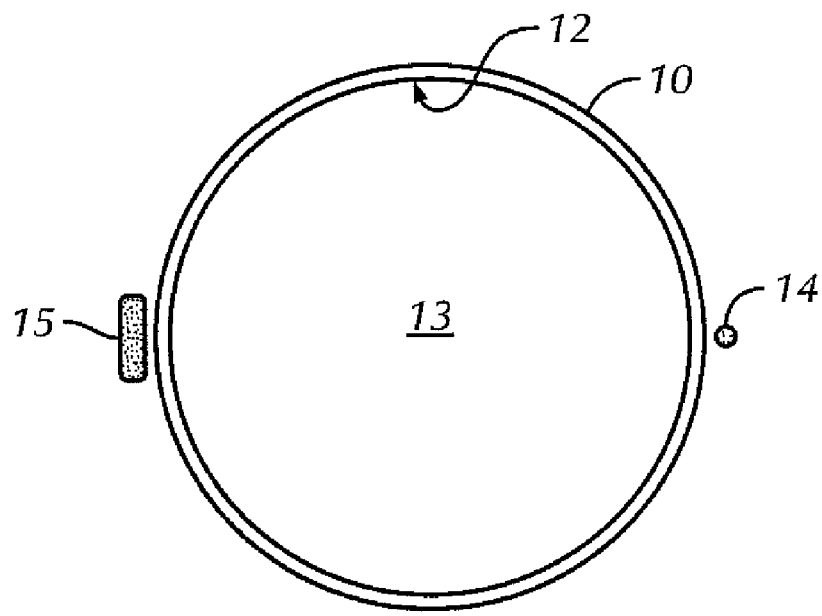
FIG. 1 is a simplified schematic drawing of a prior-art through-transmission gamma-ray densitometer.

In one aspect, embodiments disclosed herein relate to measurement of the density, level and/or interface of a fluid in a vessel using gamma rays. In other aspects, embodiments disclosed herein relate to measurement of the density, level and/or interface of a fluid in a vessel using gamma rays where the vessel is greater than 1 meter in diameter. In particular, embodiments disclosed herein relate to measurement of the density, level and/or interface of a fluid in a vessel by detecting the intensity of gamma rays backscattered by the fluid from a gamma-ray source.

As used herein, "backscatter" may refer to the deflection of gamma rays from the original direction. In some embodiments, the backscatter may be isotropic, such as where the gamma rays are scattered randomly in various directions. Backscattering occurs due to Compton scattering.

As used herein, "fluid" refers to liquids and liquid-entrained solids and gases that may be contained within a vessel. Fluids may include aqueous liquids, organic liquids, single-phase systems, and multi-phase systems such as foams, emulsions, slurries, and fluidized particles.

As used herein, "vessel" refers to a device for holding, transporting, or otherwise processing one or more fluids, for example, a container, a drum, a tank, a pipe, or a piping component. In some embodiments, a vessel may have one or more walls. In other embodiments, a vessel may be fully-enclosed. In yet other embodiments, a vessel may have one or more inlets and/or one or more outlets for transporting a fluid, for example one or more bores. In some embodiments, a vessel may operate at or below atmospheric pressure. In other embodiments, a vessel may operate at an above-atmospheric pressure. In yet other embodiments, a vessel may contain a gas or vapor, for example, air, above the one or more fluids. One skilled in the art would recognize that other embodiments of a vessel may also be used.

As used herein, "level" refers to a relative height of one or more fluids located directly below a gas or vapor material, for example, air, in a vessel. In some embodiments, the level may refer to the relative height of a boundary between a higher-density fluid and a lower-density air or vapor in a vessel. In other embodiments, the level may refer to the height of a single fluid below a gas or vapor material in a vessel. In yet other embodiments, the level may refer to the combined height of one or more vertically stacked or stratified fluids, where the lightest of the one or more fluids is heavier than the gas or vapor material, for example, air, in a vessel.

In some embodiments, the level may refer to the height of a boundary between a liquid and vapor. In other embodiments, the level may refer to the height of a boundary between a solid and vapor. In yet other embodiments, the level may refer to the height of a boundary between a liquid containing entrained solids and/or gases, and vapor. One skilled in the art would recognize that other level embodiments may also be used.

As used herein, "interface" refers to a relative height of a boundary between one or more lower-density fluids with respect to one or more higher-density fluids located proximately within a vessel. Each of the one or more fluids at an interface may be in form of a layer, foam, emulsion, suspension, or slurry. In some embodiments, the interface may be a clearly pronounced boundary, for example, a boundary between two immiscible fluid layers. In other embodiments, the interface may be an arbitrarily defined boundary, where the density of a stratified fluid changes from low to high in an uninterrupted continuum. For example, a density-based interface may be arbitrarily defined in a solid suspension, where the solids gradually settle, thus creating a higher-density fluid towards the bottom of a vessel.

In some embodiments, the interface may refer to a boundary between two liquids. In other embodiments, the interface may refer to a boundary between a liquid and a solid. In yet other embodiments, the interface may refer to a boundary between a liquid containing entrained solids and/or gases, and a liquid or a solid. One skilled in the art would recognize that other interface embodiments may also be used.

As used herein, "diameter" refers to the effective diameter of a vessel, regardless of vessel geometry. Although the specification and figures indicate cylindrical vessels, one skilled in the art would appreciate that the gamma-ray backscatter measurement systems described herein may be used with vessels of other geometries.

Figure 2:
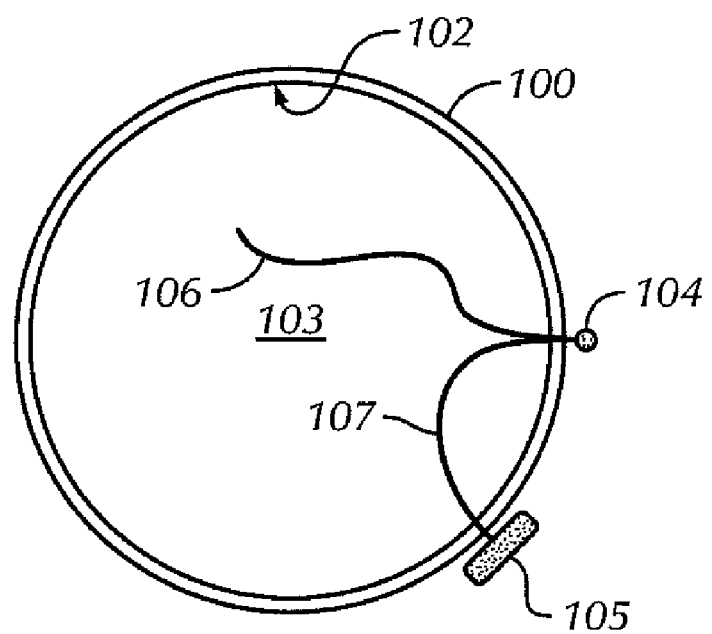
FIG. 2 is a schematic drawing of a gamma-ray density measurement system according to embodiments disclosed herein.

Referring now to FIG. 2, one example of a gamma-ray density, level and/or interface measurement instrument is illustrated. A tubular vessel 100 may have a bore 102 through which one or more fluids 103 are caused to flow. At least one source of gamma radiation 104 may be located proximate to pipe or vessel 100, and a gamma radiation detector 105 may be positioned to detect gamma rays backscattered from the at least one gamma-ray source 104.

A percentage of the gamma rays emitted by the gamma-ray source 104 may be absorbed or attenuated by the vessel 100 and the one or more fluids 103 and do not reach the gamma-ray detector 105. For example, a gamma ray may follow path 106, undergoing one or more scatterings off an atomic electron, eventually being absorbed or dissipating in energy, failing to reach detector 105.

A portion of the gamma rays emitted by source 104 may be deflected, with or without attenuation, thus reaching detector 105. For example, a gamma ray may follow path 107, undergoing one or more scatterings, eventually reaching detector 105. The rate at which gamma rays reach detector 105 may be related to the density of the one or more fluids 103 through which the gamma rays must pass to reach the detector 105 and the intensity of the source 104.

Figure 4:
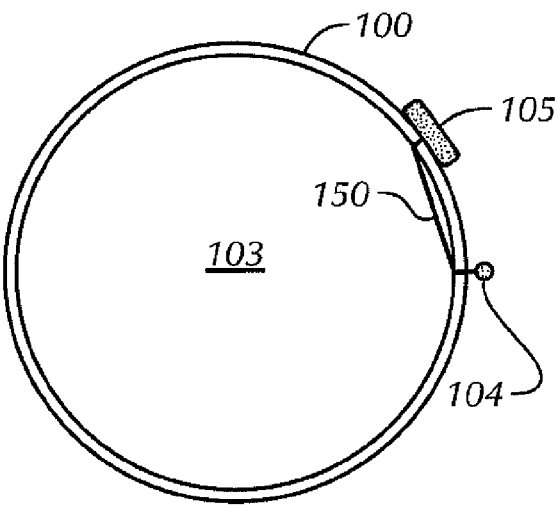
FIG. 4 is a schematic drawing depicting one potential path a backscattered gamma ray may take in reaching a gamma-ray detector according to embodiments disclosed herein.
Figure 5:
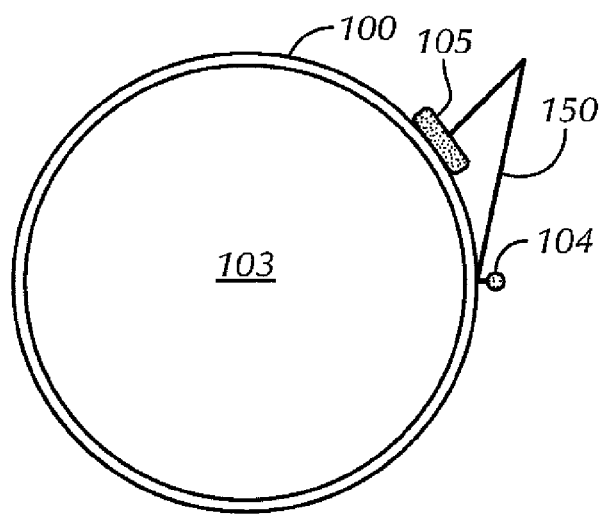
FIG. 5 is a schematic drawing depicting one potential path a backscattered gamma ray may take in reaching a gamma-ray detector according to embodiments disclosed herein.
Figure 6:
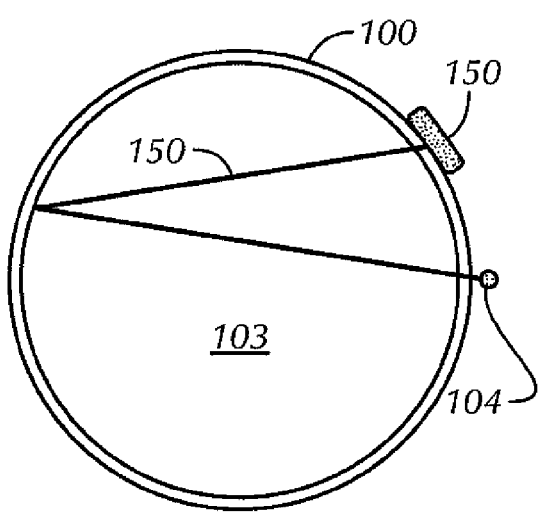
FIG. 6 is a schematic drawing depicting one potential path a backscattered gamma ray may take in reaching a gamma-ray detector according to embodiments disclosed herein.

Referring now to FIGS. 3-6, gamma rays may reach the detector through various mechanisms. Gamma rays may travel varied paths 150, which may be roughly categorized as follows: scattering in the fluid (FIG. 3); scattering in the vessel walls (FIG. 4); scattering outside the vessel (FIG. 5); scattering from the opposite wall (FIG. 6). Scattering from the opposite wall, as illustrated in FIG. 6, generally happens only at very low fluid densities, such as through air, for example.

Figure 3:
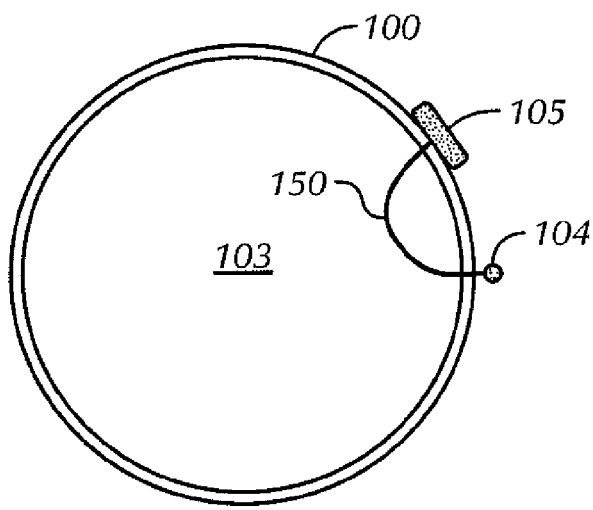
FIG. 3 is a schematic drawing depicting one potential path a backscattered gamma ray may take in reaching a gamma-ray detector according to embodiments disclosed herein.

Scattering from outside the vessel, as illustrated in FIG. 5, may be a significant portion of the total gamma-ray count for high density fluids (sand), and may also be considerable for intermediate density fluids. Scattering in the walls, as illustrated in FIG. 4, may occur for low density fluids, but is typically not present for high density fluids. Scattering in the material, as illustrated in FIG. 3, is dominant for intermediate density fluids (0.2-0.8 g/cc).

Gamma-ray backscatter measured by the detector may include each of the above described backscatter events in some embodiments. In other embodiments, shielding may be used to prevent or minimize the amount of backscatter from one or more events other than scattering from the fluid. For example, the source, the detector, or both, may be appropriately shielded to prevent scatter from outside the vessel reaching a detector.

As previously stated, the rate at which gamma rays reach the detector may be related to the density of one or more fluids through which the gamma rays must pass to reach the detector and the intensity of the source. In addition, the rate at which gamma rays reach the detector may also depend on the nominal vessel wall thickness and any changes in the effective wall thickness due to deterioration or material build-up over time. In order to maintain good metering accuracy, a gamma-ray instrument must account for these changes.

Deterioration of the vessel walls may occur via various mechanisms that may include corrosion, erosion, and other forms of degradation. As the vessel wall deterioration progresses, the total amount of material for the gamma rays to travel through decreases, and thus the counting rate increases, all else held constant. The rate of degradation of a vessel wall may depend, for example, on the nature of the process, the type of fluid service, the vessel material, the quality of vessel fabrication, and the operating conditions, including temperature and pressure. In some embodiments, the wall deterioration rate in vessels handling relatively clean, non-corrosive fluids at ambient conditions may be negligible. In other embodiments, the wall deterioration rate, for example, in a metal vessel handling highly-corrosive and erosive fluids at high temperature and pressure, may be as high as a fraction of an inch to several inches per year.

More specifically, many metal vessels are susceptible to various corrosion mechanisms. For example, metal corrosion in vessels may be internal or external; uniform or isolated, and may occur at normal or accelerated rates.

Many industrial applications distinguish between normally anticipated corrosion rates, as measured by an annual corrosion allowance, and accelerated corrosion rates that typically happen on an unplanned basis due to poor equipment maintenance, an operating excursion, or an accident.

Whereas corrosion deterioration is caused by chemical attack, vessel walls may also deteriorate due to physical wear or damage. For example, vessel wall erosion typically involves contact with abrasive fluids, such as slurries having high solids content, travelling at high velocities through the vessel. Erosion may also arise in vessel wall areas that are in contact with directly impinging fluids, for example, directly opposite from a horizontal vessel inlet nozzle. To mitigate this type of erosion problem, many process vessels are equipped with deflector plates. Other erosion problems inside a vessel may arise due to flow maldistribution generating high velocity areas, or in areas where a fluid suddenly changes direction or flashes, for example, the vessel wall adjacent to an inlet throttling valve or a sharp inlet piping elbow.

An opposite problem occurs when material build-up, for example, scale, slag, corroded metal, or polymer, generates on the inside of the vessel walls over time. For example, uncombusted hydrocarbons, such as petroleum coke, salts, and metals in many refining units can accumulate along the vessel walls as scale and slag. The build-up increases the total amount of material for the gamma rays to travel through, and thus reduces the counting rate, all else held constant.

Figure 7:
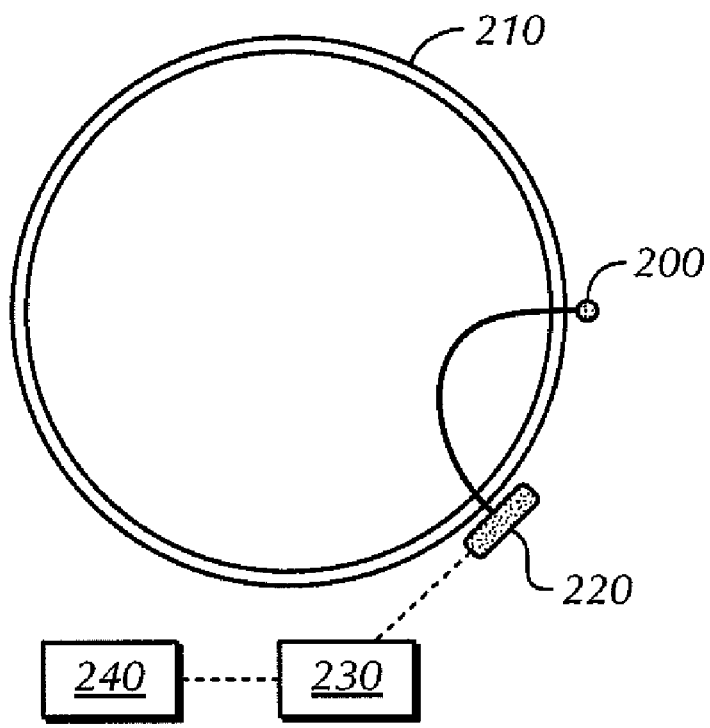
FIG. 7 is a schematic drawing of a gamma-ray density measurement system according to embodiments disclosed herein.

Referring now to FIG. 7, one embodiment of the gamma-ray backscatter instrument for measuring the density, level and/or interface coupled to a computer or a digital control system ("DCS") is illustrated. One or more gamma-ray sources 200 may be distributed along the circumference of or distributed axially along the height of vessel 210. One or more gamma-ray detectors 220 may be positioned relative to the sources 200 to detect gamma rays backscattered from the corresponding source. Use of multiple sources and/or detectors may allow for a more accurate determination of fluid properties, for example, the density, level and/or interface, as will be described below.

The one or more detectors may be coupled to a rate meter 230. Rate meter 230 may convert pulses of energy produced by detectors 220 to a DC signal which is proportional to the gamma-ray detection rate. The rate at which the gamma rays are detected will be a function of the density of one or more fluids proximate the detector 230 and the corresponding source 200.

In some embodiments, the DC signal may be used to calculate fluid density. In other embodiments, the DC signal may be used to determine fluid level and/or interface position. In yet other embodiments, the DC signal may be used to determine one or more of fluid density, level and/or interface. In some embodiments, the density, level, and/or interface position may be interpolated based on a calibration curve and the DC signal using a computer or digital control system (DCS) 240. In other embodiments, the DC signal may be used to initially determine a bulk fluid density of one or more fluids and/or gas located between the source and the detector that may be further used to calculate fluid level and/or interface. One or ordinary skill in the art would recognize that other methods for determining fluid density, level and/or interface using a DC signal generated by a gamma-ray backscatter detector may also be used.

A computer or DCS 240 may be used to generate a display of one or more of the DC signal, the fluid density, level, and/or interface corresponding to the measured detection rate of gamma-ray backscatter.

Location of the gamma-ray detectors with respect to the gamma-ray sources along the vessel wall may also vary depending on the type of measurement the instrument is primarily targeted.

With regard to gamma-ray backscatter densitometers, both axial and radial arrangements of the detectors with respect to the sources may be used. In some embodiments for measuring the bulk fluid density, one gamma-ray detector located radially with respect to a gamma-ray source may be sufficient to provide a representative fluid density measurement.

However, in many applications, fluid density may vary within the interior of vessel 200, radially and/or axially. The limited vicinity over which a backscatter meter as described herein may measure density may not always provide an accurate representation of the bulk fluid density, such as where flow turbulence does not provide for a well mixed fluid. Depending on the specific process, multiple sources and/or detectors may be placed radially and/or axially with respect to one another. Where more than one detector 230 is placed along vessel 210, the interpolated or otherwise measured density values returned by DCS 240 may be averaged. The averaged density value may be a more accurate representation of the bulk fluid density as the multiple detectors only measure the density of the fluid in a limited vicinity proximate to the source(s) and the detectors.

With regard to gamma-ray backscatter fluid level measurement, a vertical arrangement between a source and a detector may be used. In order to produce a reading within the instrument span, the fluid level in a vessel must be vertically located between the gamma-ray source and the gamma-ray detector. As the signal absorption or attenuation by a vapor or a gas is in most cases negligible, the intensity of the signal received by the detector will vary, depending on the fluid level. Specifically, the higher the fluid level between the source and the detector, the more resistance there is for a gamma-ray signal to travel through, and, thus, the weaker the signal count or intensity received by the detector.

Referring now to FIG. 13*a*, a gamma-ray fluid level measurement system is illustrated, where detector 505*a* is located vertically above source 504*a* along vessel wall 500*a*. Where fluid level 501*a* is located between fluid 503*a* and vapor or gas 502*a*, the gamma rays must predominantly travel through both fluid 503*a* and vapor or gas 502*a*. In some embodiments, a gamma-ray backscatter level instrument may directly measure fluid level using the gamma-ray count intensity received by the detector and transformed into a DC signal. In other embodiments, the level instrument may interpolate a DC signal produced from the gamma-ray count received by the detector to measure fluid level. In yet other embodiments, a gamma-ray backscatter level instrument may measure a bulk fluid density and compare it to a calibrated density of fluid 503*a* to calculate fluid level. For example, the ratio of the measured bulk fluid density to the calibrated density of the fluid 503*a* will be a function of the ratio of the portion of vertical span between source 504*a* and detector 505*a* occupied by the fluid 503*a* to the total vertical span. One of ordinary skill in the art would recognize that other methods for determining fluid level based upon gamma-ray count may also be used.

With regard to gamma-ray backscatter fluid interface measurement, a vertical arrangement between a source and a detector is also preferred. Similar to the level location for a fluid level measurement, the fluid interface in a vessel must also be vertically located between the gamma-ray source and the gamma-ray detector to produce a fluid interface measurement within the instrument span. The main distinction between a fluid level and a fluid interface measurement is that for an interface measurement, the gamma-ray signal must pass through at least two different fluids across an interface, but not through a vapor or gas phase. The two or more fluids at an interface will typically have different densities, and thus the intensity of the signal received by the detector will vary, depending on the relative amount of one or more lighter fluids above the interface and the one or more heavier fluids below the interface. Specifically, the greater the amount of the heavier fluids between the source and the detector, the weaker the signal intensity received by the detector.

Referring now to FIG. 13*b*, a gamma-ray interface measurement system is illustrated, where detector 505*b* is located vertically above source 504*b* along vessel wall 500*b*. Where fluid interface 501*b* is located between one or more heavier fluids 503*b* and one or more lighter fluids 502*b*, the gamma rays must predominantly travel through both. In some embodiments, a gamma-ray backscatter interface instrument may directly measure fluid interface using the gamma-ray count or intensity received by the detector and transformed into a DC signal. In other embodiments, the interface instrument may interpolate a DC signal produced from the gamma-ray count received by the detector to measure fluid interface. In yet other embodiments, the interface instrument may measure a bulk fluid density and compare it to a calibrated density of one or more heavier fluids 503*b* and/or one or more lighter fluids 502*b* to calculate fluid interface. For example, the measured bulk fluid density can be interpolated between the calibrated densities of one or more heavier fluids 503*b* and one or more lighter fluids 502*b*, respectively, to determine the location of fluid interface 501*b* along the vertical span between source 504*b* and detector 505*b*. One of ordinary skill in the art would recognize that other methods for determining a fluid interface based on gamma-ray count may also be used.

Referring now to FIGS. 8, 9*a*-9*b*, and 14, measurement systems are illustrated where one or more sources are combined with one or more detectors to provide multiple measurements of the density, level and/or interface of a fluid within a vessel.

Figure 8:
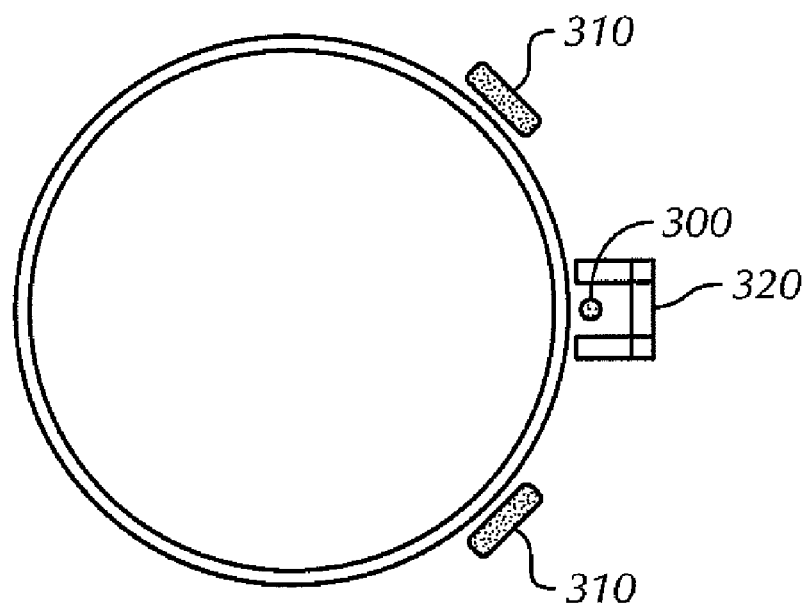
FIG. 8 is a schematic drawing of a gamma-ray density measurement system using two detectors and one source spaced circumferentially according to embodiments disclosed herein.

As illustrated in FIG. 8, a gamma-ray backscatter densitometer may include a gamma-ray source 300 spaced circumferentially from two gamma-ray detectors 310. Shielding 320 may be provided between gamma-ray source 300 and gamma-ray detectors 310. In this manner, gamma-ray backscatter density measurements may be obtained for the fluid in two areas of the vessel 330 using only one gamma-ray source 300. Alternatively, or cooperatively with circumferentially spaced gamma-ray detectors 310, gamma-ray detectors may be spaced circumferentially or axially from gamma-ray source 300 to provide density measurements for the fluid in the vessel 330.

As illustrated in FIGS. 9*a* (top view) and 9*b* (profile view), multiple sources 400 may be positioned axially and circumferentially along vessel 410 to measure the density, level and/or interface of a fluid. One or more detectors 420 may be correspondingly located to measure backscatter of gamma rays from source 400. Shielding (not shown) may be provided to minimize cross-talk between the various sources and detectors. Additionally, based upon calibrated density of one or more fluids and the vessel diameter, the detectors may be spaced such that transmission and/or backscatter of gamma rays from one source to a detector is minimized or avoided.

As described above, the detectors may be positioned to detect gamma rays backscattered from a source. In some embodiments, detectors may be positioned relative to a source so as to detect gamma rays backscattered from a source, and positioned such that through-transmission gamma rays reaching the detector are minimal or non-existent.

As illustrated in FIGS. 9a and 9b, multiple sources 400 may be positioned axially and/or circumferentially with respect to multiple detectors 420 along vessel 410 to measure one or more of the density, level and/or interface of a fluid. For example, the gamma-ray signal received by each of multiple detectors 420 may be used to calculate one or more of the density, level and/or interface of a fluid. In some embodiments, axial and/or circumferential arrangement of source/detector may be used to calculate fluid density. In other embodiments, axial source/detector arrangement may be used to calculate fluid level and/or fluid interface.

As illustrated in FIG. 14, fluid level and/or fluid interface measurements may be conducted using one or more sources 604 axially located with respect to multiple detectors 605-608 along vessel wall 600. The gamma rays from one or more sources 604 may travel through one or more fluids 603 and through either one or more fluids 602 (interface measurement) or vapor or gas 602 (level measurement) prior to being received by one or more of the multiple detectors 605-608. For example, one or more detectors 605-606 may be located above source 604, and one or more detectors 607-608 may be located below source 604 in order to measure both high and low fluid level and/or fluid interface in the vessel. Detectors 605 and 607 located closest to source 604 may be referred to as "inner" detectors, whereas detectors 606 and 608 located furthest way from source 604 may be referred to as "outer" detectors. In one specific embodiment, the inner detector 605 may be used to measure a high fluid level and/or fluid interface and the outer detector 606 may be used to measure a high-high fluid level and/or fluid interface. In another specific embodiment, the inner detector 607 may be used to measure a low fluid level and/or fluid interface and the outer detector 608 may be used to measure a low-low fluid level and/or fluid interface.

For example, when fluid level and/or fluid interface is between source 604 and detector 605, the signal intensity received by both detectors 605 and 606 will continue to change as fluid level and/or fluid interface increase. However, when fluid level and/or fluid interface is between detector 605 and detector 606, only the signal intensity received by detector 606 will continue to change as fluid level and/or fluid interface increase, while detector 605 reading will remain constant. In a similar fashion, detectors 607 and 608 will detect fluid level and/or fluid interface between source 604 and detector 607, and between detector 607 and detector 608, respectively.

The spacing between source 604 and detectors 605-608, or the instrument span, may depend upon a number of parameters, including: the density of the one of more fluids 603; vessel size, wall thickness and potential for buildup on the wall; the intensity of the one or more gamma-ray sources 604; and the minimum required accuracy for the type of measurement to be performed. As a general rule, the measurement accuracy of a gamma-ray instrument decreases with the increased spacing between the source and the detector.

In some embodiments, an instrument span may be equal to the spacing between the source 604 and one of the outer detectors 606 and 608. In other embodiments, an instrument span may be equal to the spacing between the outer detector 606 and the outer detector 608.

In some embodiments, the instrument span may be between about 20 m and 0.1 m. In other embodiments, the instrument span may be between about 15 m and 0.1 m. In yet other embodiments, the instrument span may be between about 10 m and 0.1 m. In yet other embodiments, the instrument span may be between about 8 m and 0.1 m. In other embodiments, the instrument span may be between about 5 m and 0.1 m.

The spacing between the inner detectors 605 and 607 and the outer detectors 606 and 608, respectively, and the spacing between the inner detectors 605 and 607 and the source 604 may vary accordingly. In some embodiments, the inner detector 605 and 607 spacing may be between about 20 m and 0.1 m. In other embodiments, the inner detector 605 and 607 spacing may be between about 10 m and 0.1 m. In yet other embodiments, the inner detector 605 and 607 spacing may be between about 5 m and 0.1 m.

As previously discussed, a gamma-ray through-transmission measurement of the density, level or interface of a fluid may be affected by changes in the effective vessel wall thickness over time, for example, due to wall build-up and/or degradation. The build-up or degradation affects the total amount of material the gamma rays must travel through, and thus affects the intensity of the gamma rays received by detector. Over time, the wall build-up and/or degradation can introduce significant error into the gamma-ray measurement of density, level and/or interface of a fluid in a vessel.

The problems regarding variations in wall thickness due to build-up and/or deterioration may be addressed by using gamma-ray backscatter measurement instruments with two or more detectors proximately placed along a vessel. For example, in a d3ensity, fluid level, and/or fluid interface measurement, an "outer" detector may be placed directly above an "inner" detector. As the effective wall thickness changes due to build up or deterioration over time, the gamma-ray signal count received by each detector may go up or down considerably. However, as the gamma ray signals received at both the inner and the outer detector must go through the same effective wall thickness, the wall build-up and/or deterioration will affect the signal count or intensity received by both the detectors in approximately an equal proportion. Thus, the ratio of the signal counts received by each detector stays approximately constant with changes in the effective vessel wall thickness.

Although the count ratio will remain constant with the variations in the effective wall thickness, the count ratio will still be a function of the type and/or the amount of fluid between the source and the detectors. Thus, in services where significant variation in the effective vessel wall thickness is expected, for example, due to wall build-up or deterioration, using the count ratio between the inner and the outer detector instead of the individual signal counts may be beneficial for measuring fluid properties, for example, the density, level and/or interface. As a trade-off, the precision obtained from using a signal count ratio instead of gamma-ray signal intensity may not be as high. However, the precision obtained from using a signal count ratio may still be sufficiently good for measuring fluid properties, for example, density, level and/or interface.

In selected embodiments, a gamma-ray source may be spaced circumferentially from a corresponding gamma-ray detector, where the angle $\beta$ ($\beta 1$ or $\beta 2$) between gamma-ray source and gamma-ray detector may be 90 degrees or less, as illustrated in FIG. 10a. The angle $\beta$ may be 75 degrees or less in other embodiments; 60 degrees or less in other embodiments; 45 degrees or less in other embodiments; 30 degrees or less in other embodiments; and 15 degrees or less in yet other embodiments.

In some embodiments, a gamma-ray detector may be spaced axially from a corresponding gamma-ray detector, where the angle θ (θ1 or θ2) may be 60 degrees or less, as illustrated in FIG. 10b. The angle θ may be 45 degrees or less in other embodiments; 30 degrees or less in other embodiments; and 15 degrees or less in yet other embodiments.

Where more than one gamma-ray detector is placed relative to a corresponding gamma-ray source, the angles θ, β between the source and the corresponding detectors may be the same or different, such as angles β1 and β2 illustrated in FIG. 10a and angles θ1 and θ2 in FIG. 10b. In some embodiments, the multiple gamma-ray detectors may be placed on the same side of the gamma-ray source; in other embodiments, gamma-ray detectors may be placed on opposite sides of the gamma-ray source.

In addition to obtaining an average density value, as described above, use of multiple detectors along the circumference or height/length of pipe or vessel 200 may be used to generate a profile of a fluid in pipe or vessel 200. For example, as illustrated in FIGS. 9a and 10a, circumferentially spaced detectors may provide an indication of a density variance between angular sections of pipe or vessel 200, such as a quadrant or an octant. As another example, as illustrated in FIGS. 9b and 10b, axially spaced detectors may provide an indication of an axial density gradient.

Measurement of axial and/or radial density gradients may provide an indication of the degree of settling or mixing that may be occurring in vessel or pipe 200. For example, an axial density gradient may indicate the degree of settling of a solid from a suspension contained in a vessel 200. As another example, various radial density gradients may be indicative of static, laminar, or turbulent flow in a pipe 200. Where pipe or vessel 200 forms a component in a process, one or more process variables may be manipulated in response to the density profile, such as to increase mixing or to decrease settling rates, for example.

The source of gamma rays may include cesium-137, americium-241, radium-226, iridium-192, and cobalt-60. In some embodiments, the activity of the source may range from 0.1 mCi to 10 Ci. In other embodiments, the activity of the source may be less than 5 Ci; less than 2 Ci in other embodiments; and less than 1 Ci in yet other embodiments.

Due to the measurement of backscatter as opposed to conventional through-transmission, the activity of the source may be minimized while providing measurement of density, level, or interface position of fluids in a vessel. In some embodiments, a similar size source may be used for vessels ranging in size from 1 meter to 10 meters in diameter. In other embodiments, a similar size source may be used for vessels ranging in wall thickness from 0.01 inches to 6.0 inches or more.

In selected embodiments, density, level, and interface measurements as disclosed herein may be obtained by gamma-ray backscattering by irradiating a vessel having a diameter of greater than 1.5 meters with one or more gamma-ray sources having an intensity of less than 2 Ci; less than 1 Ci in other embodiments; less than 500 mCi in other embodiments; less than 100 mCi in other embodiments; and less than 10 mCi in yet other embodiments. In other embodiments, density, level, and interface measurements as disclosed herein may be obtained by gamma-ray backscattering by irradiating a vessel having a diameter of greater than 3 meters with one or more gamma-ray sources having an intensity of less than 2 Ci; less than 1 Ci in other embodiments; less than 500 mCi in other embodiments; less than 100 mCi in other embodiments; and less than 10 mCi in yet other embodiments.

Gamma-ray detectors useful in embodiments disclosed herein may include scintillators such as sodium iodide, cesium iodide, and plastic scintillators. In some embodiments, gamma-ray detectors may include electron photo multiplier tubes. In other embodiments, gamma-ray detectors may include plastic scintillators, such as a polyvinyl toluene (PVT) scintillator, for example. In yet other embodiments, gamma-ray detectors may include ionization chambers, Geiger counters, proportional counters, semiconductors or other detectors suitable for detection of gamma rays. Where embodiments of the measurement system disclosed herein contain more than one detector, the detectors may be of the same or different types of gamma-ray detectors.

Gamma-ray backscatter density meters in accordance with embodiments disclosed herein may measure the density of a fluid in a vessel, where the density of the fluid may range from 0.05 g/cc to 7.0 g/cc. The effective density range may be from 0.1 g/cc to 4.0 g/cc in other embodiments; and from 0.2 to 2.0 g/cc in yet other embodiments. In other embodiments, one or more gamma-ray backscatter density meters may be used in conjunction with one or more gamma-ray through-transmission density meters.

In yet other various embodiments, the density of a fluid in a pipe or vessel may be controlled by manipulating one or more process variables based upon the measured density. For example, where a pipe or vessel forms a component in a process, one or more process variables may be manipulated in response to the gamma-ray backscatter density measurement of the fluid in the pipe or vessel.

The gamma-ray backscatter density gauges described above may be used to measure the density of a fluid in a vessel. Prior to use of the gauge during operation or production, the gamma-ray backscatter gauge may be calibrated. Multiple fluids of known density may be passed through a vessel, where the same vessel or a similar to the vessel for which the gauge will measure the density of the contents during operation. Gamma-ray counts for the known density fluids may be determined and recorded, developing a density calibration curve (count profile). Then, when used during production or operation, measured gamma-ray counts may be compared to the density calibration curve to determine the density of the fluid; the density of the fluid may be interpolated based upon the intensity of the backscattered gamma rays.

EXAMPLES

Simulation of Gamma-Ray Backscattering

The count rate (percentage of gamma rays reaching the detector) as a function of the fluid density may be simulated for a particular vessel material and geometry, and fluid composition, wherein a Monte Carlo simulation of the Compton scattering of the gamma rays is performed and returns the count rate for an input fluid.

Figure 11:
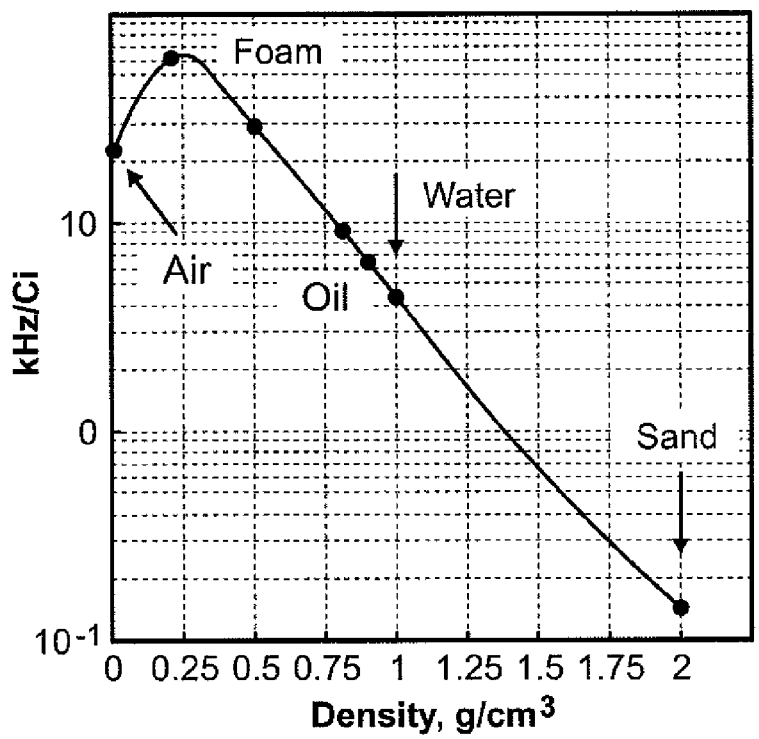
FIG. 11 is a chart depicting the rate of backscatter gamma-ray detection for various fluids based upon Monte Carlo simulations of embodiments of the gamma-ray density measurement system disclosed herein.

Referring now to FIG. 11, the simulated count rate as a function of density for a cylindrical vessel having a 2 meter diameter, 2 meters in height, with 4 cm thick steel walls is presented for a simulation using a 1 Ci $^{137}$Cs source and a 20×20 cm detector. Simulation results indicated that sand, water, heavy and light oil, and heavy and light foam may be clearly identified by gamma-ray backscattering count rates.

Figure 12A:
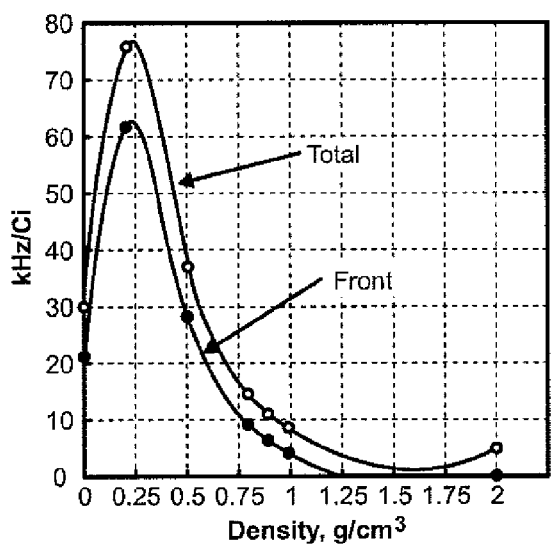
FIGS. 12a-12b are charts depicting the rate of backscatter gamma-ray detection for various fluids based upon Monte Carlo simulations of embodiments of the gamma-ray density measurement system disclosed herein.

As described above, several backscatter events may cause gamma rays to enter the detector from its back and sides, such as through scattering outside the vessel. Again, the simulation was performed for a 1 Ci $^{137}$Cs source and a 20×20 cm detector. As shown in FIGS. 12a (linear scale) and 12b (log scale), simulated results for the total rate (upper line) and the rate coming only from the front of the counter (bottom line) are illustrated. The unwanted backscatter count, or the difference in total count rate and count from the front of the detector, may be a considerable fraction of the total count, especially at high density.

Unwanted scatter events may be blocked by shielding the back and sides of the counter. Shielding the source may also effectively minimize count due to unwanted scatter. Shielding of both the source and the detector may also be done to minimize count due to unwanted scatter.

Laboratory Tests

Figure 12B:
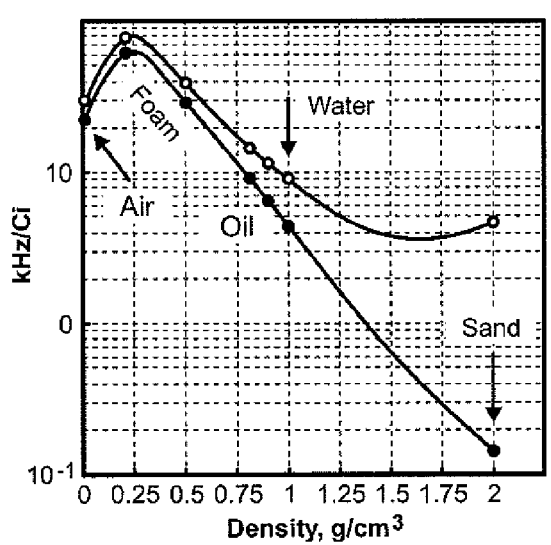

The validity of the simulation and the operational principle as a whole was tested in laboratory by altering a bucket of water and the same bucket filled with either pulverized coal or hydraulic oil. Although the measured signal ratios are not as large as in FIGS. 12a-12b, they are consistent with the ratios predicted in simulation.

In the test, a 5 mCi $^{137}$Cs source was used to irradiate a 5 gallon bucket filled with a fluid. A PVT plastic scintillator was used to detect the scattered radiation, and was placed relative to the source so as to detect gamma-ray backscatter. Sufficient shielding was placed intermediate the source and the detector to prevent transmission of gamma rays from the source to the detector, the detector count thus including only backscatter radiation. Fluids used included water, pulverized coal (from Southern Company Services, bulk density of 0.7 g/cc) and hydraulic oil (from Golden West, density of 0.9 g/cc). The buckets were filled with the desired fluid, and the count rates were measured.

In the first run, the gamma-ray detector was placed approximately at the mid height of the bucket and about 1 inch away from the bucket. In the second run, the counter was placed toward the top of the bucket and as close to the bucket as possible. The results of the first and second runs are presented in Table 1 below.

TABLE 1

| Material | Measured Count Rate (kHz/Ci) |
| --- | --- |
| Run 1 | |
| Water | 11.40 |
| Coal | 10.66 |
| Run 2 | |
| Water | 18.64 |
| Oil | 19.34 |
| Coal | 17.62 |

The results of the first and second runs indicate that gamma-ray backscatter may be effectively used to determine the density of a fluid in a vessel. The results of the first and second runs are compared to the Monte Carlo simulation results in Table 2 below.

TABLE 2

| Materials | Measured Count Ratio | Simulated Count Ratio |
| --- | --- | --- |
| Coal/Water | 0.935; 0.945 Average: 0.940 | 0.911 ± 0.02 |
| Oil/Water | 1.038 | 1.054 ± 0.017 |

The comparison of simulated results to the results of the first and second runs indicated that the measured results were within two standard deviations of the simulated results. These results may differ due to the variation in vessel composition and thickness (bucket versus 2 cm steel) as well as the relative placement of the source and the detector. Additionally, simulated and actual results may differ due to the variation in the simulated and actual chemical compositions of the coal and oil.

As illustrated by the above simulations and experiments, vessel size, material, and source/detector placement may each affect the gamma-ray backscatter count rate. Accordingly, calibration curves generated prior to operational use for each source/detector/vessel combination may provide for accurate measurement of fluid densities during operation.

In another test, a 100 mCi Cesium source and two parallel-spaced plastic scintillator detectors, and inner and an outer, are mounted on a wheel cart that is moved along a wall assembly consisting of various density materials, designed to simulate various process fluids and interfaces in a vessel. The source is used to irradiate the wall assembly, consisting of three density segments, varying from 0.6 to 1.0 g/cc. The plastic scintillator is used to detect the scattered radiation, and is placed relative to the source on a wheel cart so as to detect gamma-ray backscatter from the various wall assemblies. A ¾ inch (20 mm) steel sheet is mounted on the same wheel cart as a mock wall. One or more extra removable screens in front of the permanent steel sheet are used to simulate the wall build-up. Sufficient shielding is placed intermediate the source and the detectors to prevent transmission of gamma rays from the source to the detectors, the detectors count thus including only backscatter radiation.

In the first run, the wheel cart is moved along the wall assembly without the extra removable screen in front of the steel sheet, thus simulating vessel wall conditions with no build-up. In the second run, an extra removable 2 mm steel screen is placed in front of the 20 mm steel sheet to simulate vessel wall build-up. In the third run, an extra ½ in Teflon™ screen is placed in front of the 20 mm steel sheet to simulate vessel wall build-up.

In all three runs, the total length of the wall assembly is 400 cm, where the length of each of the three wall segments with corresponding densities of 1 g/cc, 0.7 g/cc, and 0.6 g/cc is approximately 125 cm, respectively. The remaining 25 cm segment of the 400 cm wall assembly is void and has a density of approximately 0 g/cc.

In all three runs, the inner detector is placed 32 cm horizontally apart from the source on the wheel cart along the wall. The outer detector is placed 52 cm horizontally apart from the source on the wheel cart along the wall.

The results of the first, second, and third runs indicate that gamma-ray backscatter may be effectively used to determine the density, level and/or interface of a fluid in a vessel. The results of the first and second runs are illustrated in FIG. 15.

Figure 15:
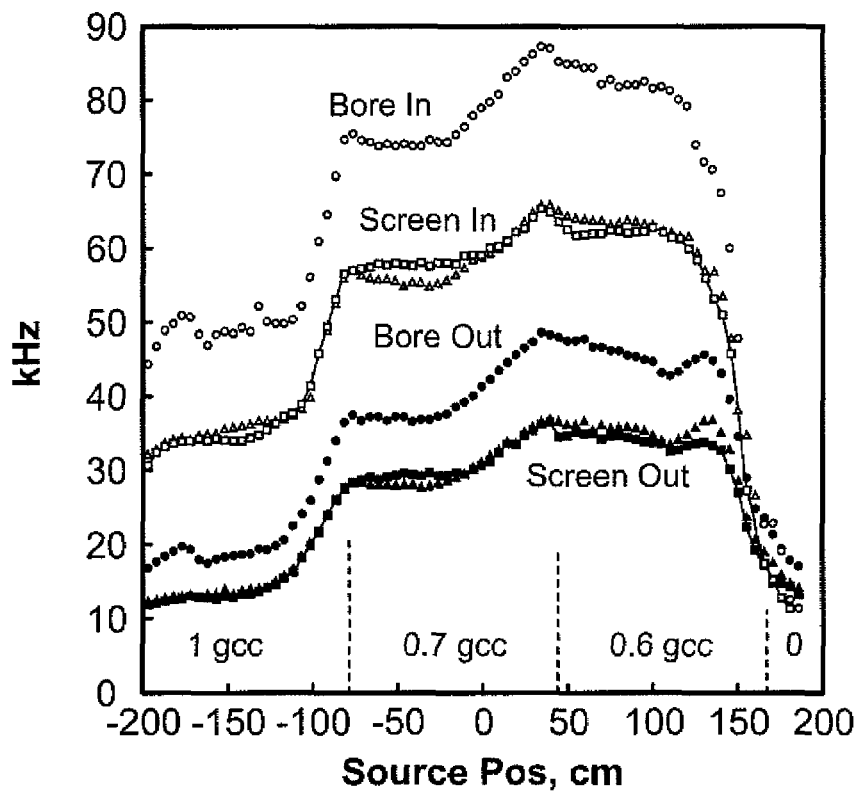
FIG. 15 is a chart depicting the gamma-ray backscatter signal intensity at the inner and the outer detectors as a function of source position along the wall.

Referring to FIG. 15, the "Bare In/Out" data points represent the signal intensity received by the inner and the outer detectors along the wall assembly in the first run, without the extra removable screen. The "Screen In/Out" data points represent the signal intensity received by the inner and the outer detectors in the second run, with the extra removable screen in place. The circles in the "Screen In/Out" plot represent data points taken with a ½ inch Teflon™ removable screen in place to simulate vessel wall build-up. The triangles in the "Screen In/Out" plot represent data points taken with a 2 mm stainless steel removable screen in place to simulate vessel wall build-up.

As illustrated in FIG. 15, a gamma-ray backscatter instrument may be useful for measurement of various fluid properties, for example, density, level and/or interface. For example, the changes in signal intensity between the wall assemblies of various densities may represent the fluid level and/or the fluid interface.

Figure 16:
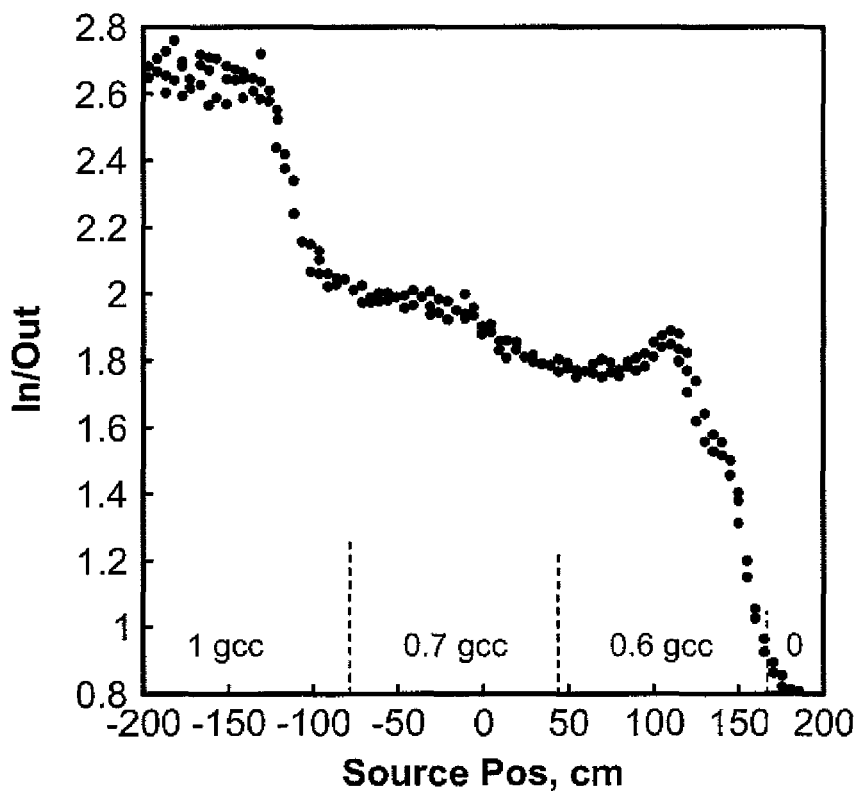
FIG. 16 is a chart depicting a count ratio between the gamma-ray signal intensity at the inner detector and the signal intensity at the outer detector as a function of source position along the wall in the first and the second experimental runs.

The counting ratio between the signal strength at each detector with respect to wall position is illustrated in FIG. 16.

Referring now to FIG. 16, the counting ratio between the signal strength at the inner and the outer detectors along the wall assembly is illustrated, both with and without an extra screen to simulate vessel wall build-up. As evident from FIG. 16, as the effective wall thickness changes, the count ratio remains constant and only varies as a function of position along the wall. Thus, the count ratio may be useful for measurement of various fluid properties, for example, density, level and/or interface.

The measurement precision of the density, level and/or interface measurement can be determined based on the slope of the signal intensity against source position graph illustrated in FIG. 15 above. For a different source size Q and integration time τ, the measurement precision a function can be described as follows:

$$\sigma \sim 1/\sqrt{(Q^*\tau)}$$

Figure 17A:
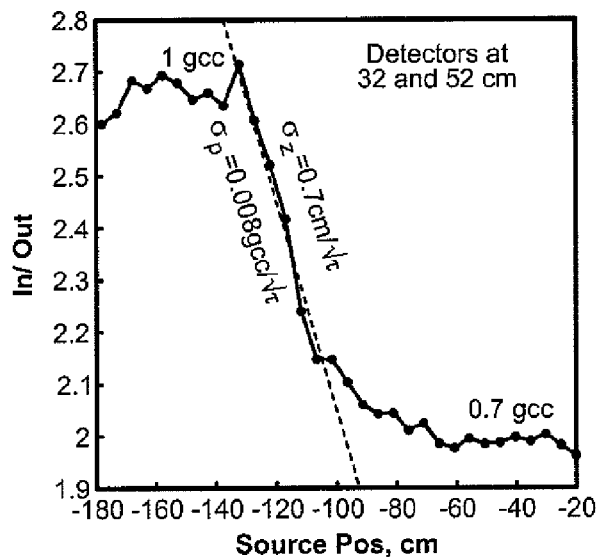
FIGS. 17a-c present charts depicting the method of determining the measurement precision from the slope of the signal intensity against source position chart in FIG. 15.
Figure 17B:
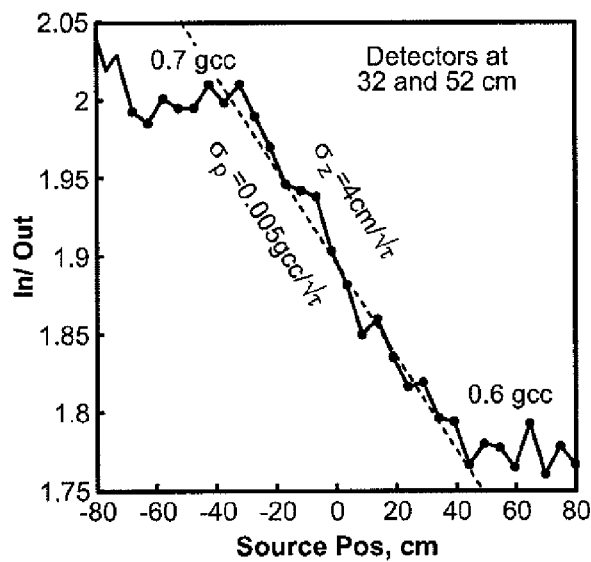
Figure 17C:
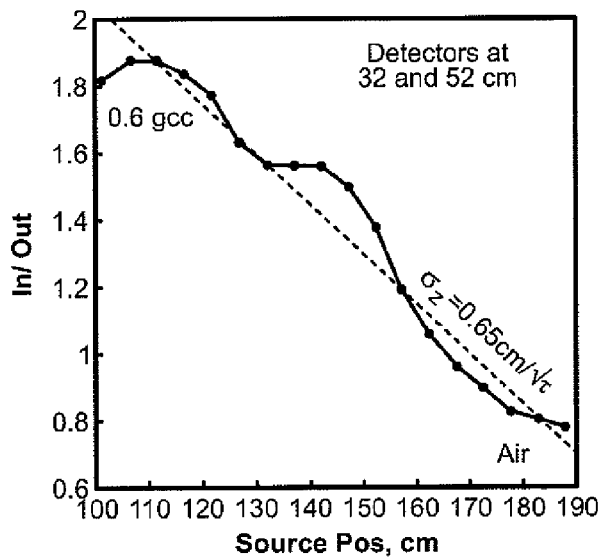

The measurement precision (σ) determination from the slope of the various portions of the signal intensity against source position graph in FIG. 15 above is illustrated in FIG. 17a-c below.

Referring to FIGS. 17a-c, the numbers quoted are normalized to 100 mCi source and 1 second integration time. As shown in FIGS. 17a-c, a density measurement error of less than +/−0.01 g/cc can be obtained with 1 second integration time. The interface error depends on the difference in density above and below the interface. The interface error is 7 mm for the density difference between the two fluids at the interface of 0.3 g/cc, and 4 cm for the density difference of 0.1 g/cc. The dynamic range for the interface and/or level is driven by the distance from the source to the outer detector. As the distance between the source and the outer detector increases, the count ratio increases, and thus the measurement precision also initially increases. However, beyond a certain distance, the signal intensity becomes so low that it cannot be precisely measured, and thus the density and/or interface measurement precision deteriorates. Thus, there may be an optimal spacing distance between the gamma-ray source and the gamma-ray detector that provides improved measurement precision. Other parameters that may affect gamma-ray measurement precision include the gamma-ray source size or the integration time.

Advantageously, embodiments disclosed herein may provide for non-contact density measurement by positioning a gamma-ray detector relative to a gamma-ray source so as to detect gamma-ray backscatter. The non-contact measurement may allow for the measurement of density, level and/or interface of a fluid, where the material is hazardous, extremely hot, or where direct contact measurements are not possible. By detecting gamma-ray backscatter, gamma rays do not have to traverse the entire vessel diameter, which may allow for the use of lower intensity gamma-ray sources as well as measurement of density, level and/or interface of a fluid in larger vessels than is current possible with through-transmission measurements.

Further, certain types of fluid properties, for example, fluid interface, may not be measurable in larger vessels using through-transmission, because both fluids at the interface may effectively absorb or attenuate the entire gamma-ray signal before it reaches the detector. Thus, using a gamma-ray backscatter instrument according to embodiments disclosed herein provides a robust alternative measurement method of certain fluid properties, for example, fluid interface in a vessel.

Because embodiments of the gamma-ray backscatter density measurements described herein may allow for use of lower intensity gamma-ray sources, cross-talk between multiple meters used within a production facility may be decreased. The use of lower intensity sources may also allow for use of more than one source and/or detector per vessel, possibly generating a more accurate reflection of fluid density due to multiple measurements. Additionally, because backscatter measurement may allow use of lower intensity gamma-ray sources, production facilities may use additional measuring devices at a single site without incurring the more stringent safety protocols required by state and federal governments for sites having moderate amounts of radioactive material.

With regard to vessel walls subject to build-up and/or deterioration, the embodiments disclosed herein provide a robust solution for measurement of density, level and/or interface of a fluid in a vessel by determining a count ratio between gamma-ray backscatter intensities received by two or more detectors. By placing two or more gamma-ray detectors proximately along the vessel wall, the ratio of the signal intensities received by each detector remains constant with changes in the effective vessel wall thickness, because each signal is equally effected by changes in the effective wall thickness. Additionally, as the two or more detectors can be proximately placed with respect to each other and the gamma-ray source along the vessel wall, the accuracy of a gamma-ray backscatter measurement using the count ratio is less likely to be effected by localized differences in the effective wall thickness inside the vessel.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

What is claimed:

1. A method to determine a fluid density in a vessel, the method comprising:
   detecting gamma rays backscattered by a fluid from a gamma-ray source positioned proximate to a vessel with at least two gamma-ray detectors positioned proximate to the vessel and to each other; and
   determining a density value of the fluid based upon intensities of backscattered gamma rays received by the two or more gamma-ray detectors;
   wherein the vessel wall is subject to at least one of buildup and deterioration.

2. The method of claim 1, the determining a density value comprising determining a ratio of intensities of the backscattered gamma rays received by any two of the two or more gamma-ray detectors.

3. The method of claim 1, wherein the two or more gamma-ray detectors are spaced vertically from the gamma-ray source and from each other a selected distance.

4. The method of claim 3, wherein the selected distance is within the range from 0.1 to 20 meters.

5. The method of claim 1, further comprising generating a calibration curve for use in the determination of the fluid density.

6. The method of claim 1, wherein the determining comprises interpolating a fluid density based upon a calibration curve.

7. The method of claim 1, further comprising converting the detected gamma-ray backscatter from the two or more gamma-ray detectors to a DC signal.

8. The method of claim 7, further comprising converting the two or more DC signals to the density value.

9. The method of claim 7, further comprising displaying at least one of the DC signals and the density value on a video display terminal.

10. The method of claim 1, further comprising controlling the fluid density in the vessel based upon the determined density value.

11. A method to determine a fluid level in a vessel, the method comprising:
   detecting gamma rays backscattered by a fluid from a gamma-ray source positioned proximate to a vessel with at least two gamma-ray detectors positioned proximate to the vessel and to each other; and
   determining a level value of the fluid based upon intensities of backscattered gamma rays received by the two or more gamma-ray detectors;
   wherein the vessel wall is subject to at least one of buildup and deterioration.

12. The method of claim 11, the determining a level value comprising determining a ratio of intensities of the backscattered gamma rays received by any two of the two or more gamma-ray detectors.

13. The method of claim 11, wherein the two or more gamma-ray detectors are spaced vertically from the gamma-ray source and from each other a selected distance.

14. The method of claim 13, wherein the selected distance is within the range from 0.1 to 20 meters.

15. The method of claim 11, further comprising generating a calibration curve for use in the determination of the fluid level.

16. The method of claim 11, wherein the determining comprises interpolating a fluid level based upon a calibration curve.

17. The method of claim 11, further comprising converting the detected gamma-ray backscatter from the two or more gamma-ray detectors to a DC signal.

18. The method of claim 17, further comprising converting the two or more DC signals to the level value.

19. The method of claim 17, further comprising displaying at least one of the DC signals and the level value on a video display terminal.

20. The method of claim 11, further comprising controlling the fluid level in the vessel based upon the determined level value.

21. A method to determine a fluid interface in a vessel, the method comprising:
   detecting gamma rays backscattered by one or more fluids from a gamma-ray source positioned proximate to a vessel with at least two gamma-ray detectors positioned proximate to the vessel and to each other; and
   determining an interface value of a fluid based upon intensities of backscattered gamma rays received by the two or more gamma-ray detectors;
   wherein the vessel wall is subject to at least one of buildup and deterioration.

22. The method of claim 21, the determining an interface value comprising determining a ratio of intensities of the backscattered gamma rays received by any two of the two or more gamma-ray detectors.

23. The method of claim 21, wherein the two or more gamma-ray detectors are spaced vertically from the gamma-ray source and from each other a selected distance.

24. The method of claim 23, wherein the selected distance is within the range from 0.1 to 20 meters.

25. The method of claim 24, further comprising generating a calibration curve for use in the determination of the interface value.

26. The method of claim 21, wherein the determining comprises interpolating an interface value based upon a calibration curve.

27. The method of claim 21, further comprising converting the detected gamma-ray backscatter from the two or more gamma-ray detectors to a DC signal.

28. The method of claim 27, further comprising converting the two or more DC signals to the interface value.

29. The method of claim 26, further comprising displaying at least one of the DC signals and the interface value on a video display terminal.

30. The method of claim 21, further comprising controlling a fluid interface position in the vessel based upon the determined interface value.

31. A system for measuring a fluid level in a vessel, the system comprising:
   at least one gamma-ray source positioned proximate to a vessel;
   at least one gamma-ray detector positioned proximate to the vessel, wherein the at least one gamma-ray detector is configured to detect gamma rays backscattered by the fluid from the at least one gamma-ray source; and
   a translator for converting the detected gamma-ray backscatter into a level value.

32. The system of claim 31, wherein the translator comprises:
   a device to convert the detected gamma rays to a DC signal; and
   a computer for converting the DC signal to the level value.

33. The system of claim 32, further comprising a display console for displaying the DC signal, the level value, or a combination thereof.

34. The system of claim 33, wherein the computer is configured to:
   receive a DC signal from each of multiple detectors;
   convert each of the DC signals to a corresponding bulk density value;
   calculate the level value using the one or more corresponding bulk density values.

35. The system of claim 34, wherein the system comprises a gamma-ray source and at least two gamma-ray detectors vertically spaced a distance within the range from 0.1 to 20 meters.

36. The system of claim 35, wherein the computer is configured to convert a ratio of signals received from the two gamma-ray detectors to the level value.

37. The system of claim 31, wherein the system comprises at least two gamma-ray sources and at least two gamma-ray detectors.

38. The system of claim 31, wherein the vessel is greater than 3.0 meters in diameter and an intensity of the gamma-ray source is less than 1 Ci.

39. A system for measuring a fluid interface in a vessel, the system comprising:
   at least one gamma-ray source positioned proximate to a vessel;
   at least one gamma-ray detector positioned proximate to the vessel, wherein the at least one gamma-ray detector is configured to detect gamma rays backscattered by the at least one of the two fluids from the at least one gamma-ray source; and
   a translator for converting the detected gamma-ray backscatter into an interface value.

40. The system of claim 39, wherein the translator comprises:
- a device to convert the detected gamma rays to a DC signal; and
- a computer for converting the DC signal to the interface value.

41. The system of claim 40, further comprising a display console for displaying the DC signal, the level value, or a combination thereof.

42. The system of claim 40, wherein the computer is configured to:
- receive a DC signal from each of multiple detectors;
- convert each of the DC signals to a corresponding bulk density value;
- calculate the interface value using the one or more corresponding bulk density values.

43. The system of claim 40, wherein the system comprises a gamma-ray source and at least two gamma-ray detectors vertically spaced a distance within the range from 0.1 to 20 meters.

44. The system of claim 43, wherein the computer is configured to convert a ratio of signals received from the two gamma-ray detectors to the interface value.

45. The system of claim 39, wherein the system comprises at least two gamma-ray sources and at least two gamma-ray detectors.

46. The system of claim 39, wherein the vessel is greater than 3.0 meters in diameter and an intensity of the gamma-ray source is less than 1 Ci.

* * * * *